United States Patent [19]

Lauritzen et al.

[11] Patent Number: 5,453,296
[45] Date of Patent: Sep. 26, 1995

[54] METHOD FOR MAKING AN ABSORBENT PRODUCT HAVING INTEGRALLY PROTECTED ADHESIVE

[75] Inventors: Nels J. Lauritzen, Piscataway; John T. Ulman, Woodbridge, both of N.J.

[73] Assignee: McNeil-PPC, Inc., Milltown, N.J.

[21] Appl. No.: 57,716

[22] Filed: May 4, 1993

[51] Int. Cl.⁶ .................... B05D 5/10; B05D 3/02; B05D 3/10
[52] U.S. Cl. .................... 427/208.6; 427/208.8; 427/271; 427/316; 427/350; 427/373
[58] Field of Search .............. 427/208.6, 208.8, 427/350, 275, 265, 152, 316, 264, 271, 373

[56] References Cited

U.S. PATENT DOCUMENTS

| | | | |
|---|---|---|---|
| 2,095,776 | 10/1937 | von Hofe et al. | 427/275 |
| 2,861,006 | 11/1958 | Salditt | 427/208.6 |
| 3,434,862 | 3/1969 | Luc | 427/152 |
| 3,913,580 | 10/1975 | Ginocchio | 128/290 W |
| 3,954,107 | 5/1976 | Chesky et al. | 128/290 R |
| 4,023,571 | 5/1977 | Comerford et al. | 128/290 P |
| 4,061,820 | 12/1977 | Magid et al. | 427/208.6 |
| 4,219,596 | 8/1980 | Takemoto et al. | 427/208.8 |
| 4,336,804 | 6/1982 | Roeder | 128/290 R |
| 4,337,772 | 7/1982 | Roeder | 128/290 R |
| 4,376,440 | 3/1983 | Whitehead et al. | 604/387 |
| 4,475,913 | 10/1984 | Hlaban | 604/387 |
| 4,587,152 | 5/1986 | Gleichenhagen et al. | 427/208.6 |
| 4,696,848 | 9/1987 | Jones et al. | 427/208.6 |
| 4,894,277 | 1/1990 | Akasaki | 427/373 |
| 4,906,492 | 3/1990 | Groshens | 427/152 |
| 4,960,619 | 10/1990 | Slautterback et al. | 427/265 |
| 5,064,492 | 11/1991 | Friesch | 427/208.2 |
| 5,250,253 | 10/1993 | Battrell | 427/208.4 |

FOREIGN PATENT DOCUMENTS

| | | | |
|---|---|---|---|
| 2054815 | 6/1992 | Canada | 427/208.6 |
| 0229639A2 | 7/1987 | European Pat. Off. | |
| 2644032A1 | 6/1978 | Germany. | |
| 1075939 | 7/1967 | United Kingdom | 427/208.6 |

*Primary Examiner*—Diana Dudash

[57] ABSTRACT

A method of making an absorbent product in which pressure sensitive adhesive is used to attach the product to a user's undergarment. The product does not require release paper to protect the adhesive from unintended contact prior to use. The product is made by forming depressions in a fluid impervious barrier so as to create raised areas in the barrier that protect the adhesive. The depressions may be formed in the garment facing surface of the barrier and the adhesive applied within the depressions so that the raised areas adjacent the depressions protect the adhesive. Alternatively, the depressions may be formed in the surface of the barrier opposite the garment facing surface so as to create raised areas in the garment facing surface and the adhesive applied adjacent the raised areas.

17 Claims, 4 Drawing Sheets

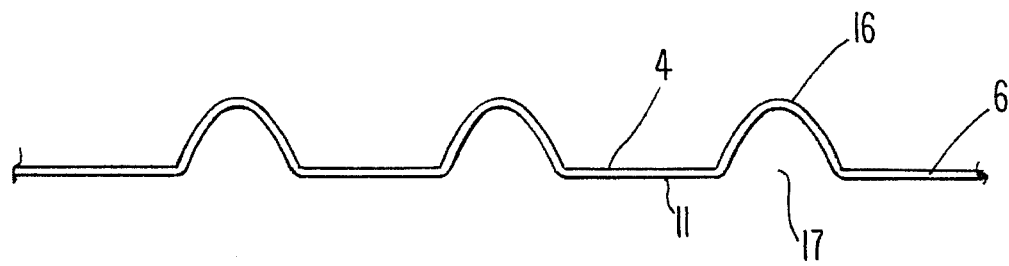
_Fig. 5a_
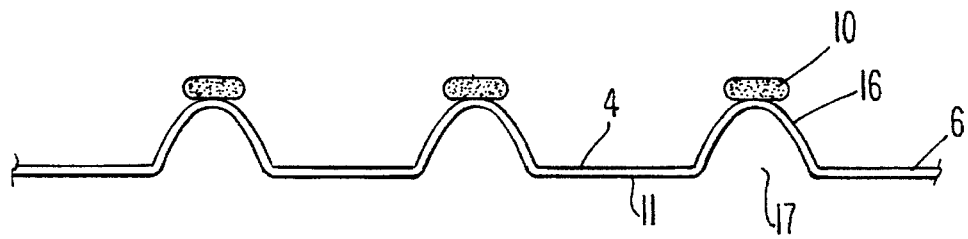
_Fig. 5b_
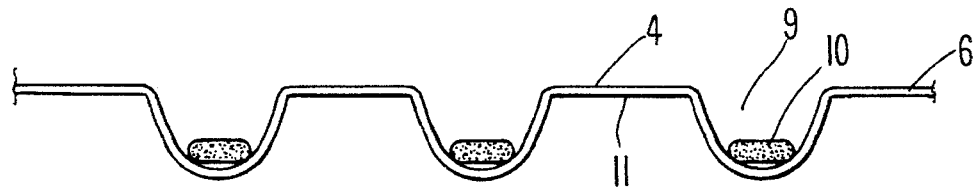
_Fig. 5c_
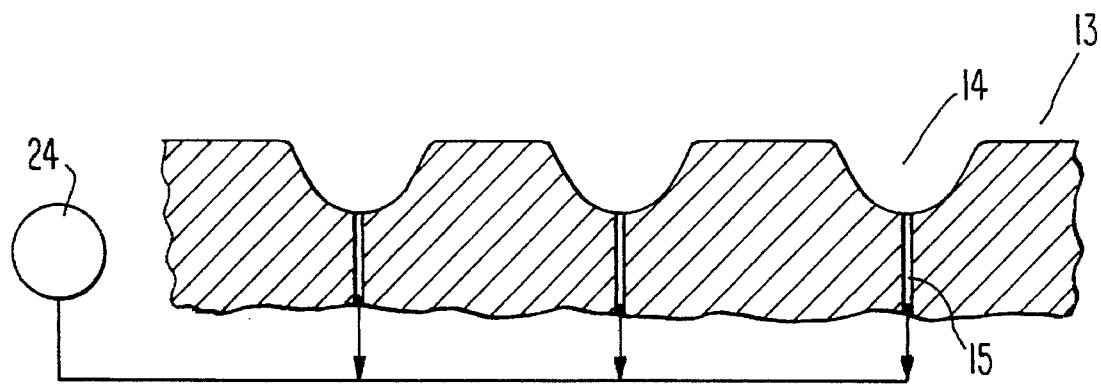
_Fig. 3_

METHOD FOR MAKING AN ABSORBENT PRODUCT HAVING INTEGRALLY PROTECTED ADHESIVE

FIELD OF THE INVENTION

The current invention is directed to absorbent products such as panty liners, sanitary napkins, incontinence pads and the like. More specifically, the current invention is directed to a method of making an absorbent product having positioning adhesive that is integrally protected by the garment facing surface of the product, thereby eliminating the need for release paper.

BACKGROUND OF THE INVENTION

Traditionally, absorbent products such as panty liners, sanitary napkins and incontinence pads have been held in place by pressure sensitive adhesive, typically a double sided tape or a hot melt type glue, disposed on the garment facing side of the pad. The pressure sensitive adhesive holds the pad in place by adhering it to the crotch of the wearer's undergarment. The pressure sensitive adhesive is covered with release paper that protect the adhesive from dirt and unintended adhesion during manufacture, packaging and storage. Typically, the release paper has been coated on one side with a coating, which may be silicone, that reduces the adherency to the adhesive of the coated side of the release paper.

Since the release paper must be removed by the user just prior to application of the product to an undergarment, its presence creates waste and complicates the utilization of the product. One approach for dispensing with the release paper, disclosed in U.S. Pat. No. 4,475,913 (Hlaban), involves folding an absorbent batt along its longitudinal edges so as to create soft edges for the product. In so doing, a centrally disposed cavity is formed that extends the length of the product. A baffle, supplied in fluid form, is then extruded into the cavity so as to conform to it and a pressure sensitive adhesive is deposited onto the portion of the baffle within the cavity. According to this reference, no release paper is need because the adhesive is shielded by the walls of the cavity.

Unfortunately, this approach suffers from a variety of drawbacks. First, the manufacturing process is complex—the edges must be folded and maintained in place during extrusion of the baffle, the amount of film extruded must be carefully controlled, and the cavity shape must be maintained in the extruded film. Second, the folding creates a thick, bulky product, whereas many users prefer a thin, less obtrusive product. Third, the cavity will generally be relatively deep, since its walls are substantially the thickness of the absorbent batt. Such depth will make it difficult for a user to bring the adhesive into contact with the under-garment unless the cavity is relatively wide, in which case the adhesive will not be adequately protected from unintended contact. Lastly, this approach limits the location of the adhesive to the longitudinal center of the product, whereas locating the adhesive around the garment facing surface in a more dispersed pattern may create a more secure attachment.

Consequently, it would be desirable to provide a method of making an absorbent product having pressure sensitive positioning adhesive in which the adhesive was adequately protected from unintended contact prior to use without the need for release paper but that allowed the user to readily attach the product to an under-garment. Moreover, it would be desirable to provide a method of making such a product without creating undue complexity in the manufacturing process and in a manner that allowed the adhesive to be dispersed around the garment facing surface in a variety of patterns.

SUMMARY OF THE INVENTION

It is an object of the current invention to provide a method of making an absorbent product having pressure sensitive positioning adhesive in which the adhesive is adequately protected from unintended contact prior to use without the need for release paper but that allows the user to readily attach the product to an undergarment. It is a further object of the invention to provide a method of making such a product without creating undue complexity in the manufacturing process and in a manner that allows the adhesive to be dispersed around the garment facing surface in a variety of patterns. These and other objects are accomplished in a method of applying and protecting positioning adhesive on an absorbent article having a fluid impervious barrier having a first surface forming a garment facing surface of such article and a second surface opposite said first surface, comprising the steps of (i) locally deforming portions of said barrier so as to form a plurality of depressions in a pattern on one of said surfaces of said barrier so as to form a corresponding raised area in the other one of said surfaces of said barrier opposite each of said depressions, and (ii) depositing an adhesive in a pattern on said first surface of said barrier.

In one embodiment of the method, the barrier has a surface opposite the garment facing surface, and the step of forming the plurality of depressions comprises forming the depressions in the surface opposite the garment facing surface so as to form the raised areas in the garment facing surface. In this method, the step of depositing the adhesive comprises the step of depositing a portion of the adhesive on the raised areas and the method further comprises the step of inverting the raised areas so as to form adhesive containing depressions in the garment facing surface and raised areas in the surface opposite the garment facing surface.

In another embodiment of the method, the barrier has a surface opposite the garment facing surface, and the step of forming the plurality of depressions comprises forming the depressions in the surface opposite the garment facing surface so as to form raised areas in the garment facing surface. In this method, the step of depositing the adhesive comprises the step of depositing the adhesive between the raised areas on the garment facing surface.

In another embodiment of the method, the step of depositing the adhesive comprises the step of depositing a portion of the adhesive in each of the depressions and the step of forming the plurality of depressions comprises forming the depressions in the garment facing surface of the barrier.

BRIEF DESCRIPTION OF THE DRAWINGS

FIG. 3 is a cross-section through a vacuum forming plate for forming depressions in the barrier of the absorbent product shown in FIG. 1.

FIG. 5a, 5b and 5c are cross-sections showing the barrier through three stages of one method of forming the depressions and applying the adhesive.

DESCRIPTION OF THE PREFERRED EMBODIMENT

Figure 1:
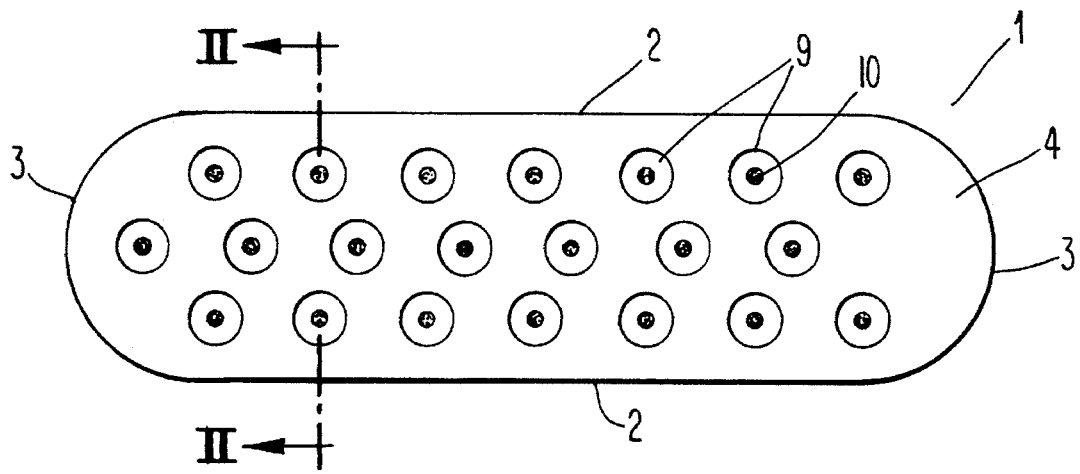
FIG. 1 is plan view of the garment facing side of a sanitary napkin according to the current invention.
Figure 2:
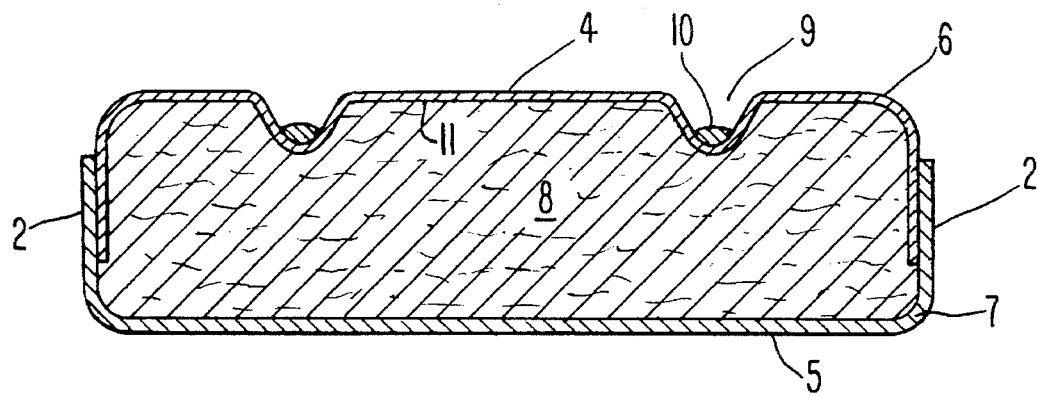
FIG. 2 is a cross-section through lines II—II shown in FIG. 1.

A sanitary napkin 1 according to the current invention is shown in FIGS. 1 and 2. The napkin 1 has a garment facing surface 4, a body facing surface 5, left and right longitudinally extending sides 2, and front and rear transverse ends 3. As shown in FIG. 2, an absorbent core 8 is disposed between the garment facing 4 and body facing 5 surfaces.

As is known in the art, the absorbent core 8 may be comprised of a loosely associated absorbent hydrophilic material such as cellulose fibers, including wood pulp, regenerated cellulose fibers or cotton fibers, or other absorbent materials generally known in the art, including acrylic fibers, polyvinyl alcohol fibers, peat moss or super-absorbent materials.

The body facing surface 5, so called because it is intended to be worn against the body of the user, is formed by a layer 7 of a body-fluid pervious material, typically referred to as a "cover." The cover 7 may be formed from any fluid pervious material that is comfortable against the skin and that permits fluid to penetrate to the underlying absorbent core 8, which retains the fluid. The cover 7 should retain little or no fluid in its structure to provide a relatively dry surface next to the skin. The fluid pervious cover 7 may be a fibrous non-woven fabric made of fibers or filaments of polymers such as polyethylene, polypropylene, polyester or cellulose. Alternatively, the cover 7 may be formed from an apertured polymeric film. The thickness of the cover 7 will vary from approximately 0.001 to 0.062 inch, depending on the material chosen.

Generally, the fluid pervious cover 7 is a single sheet of material having a width sufficient to form the body-facing surface 5 of the napkin. Preferably, the fluid pervious cover 7 is longer than the absorbent core 8 so as to form the front and rear transverse ends 3, respectively, and wider than the absorbent core so as to form the longitudinally extending sides 2. As shown in FIG. 2, the fluid pervious cover 7 may extend around the sides of the core 8 in a C-shaped configuration.

The napkin 1 further comprises a layer 6 of a body fluid impervious material, typically referred to as a "barrier." One surface of the barrier 6 forms the garment facing surface 4 and another surface 11, opposite the garment facing surface, faces toward the central absorbent 8. The impervious barrier 6 may comprise any thin, flexible, body fluid impermeable material such as a polymeric film—for example, polyethylene, polypropylene, or cellophane or a normally fluid pervious material that has been treated to be impervious, such as impregnated fluid repellent paper or non-woven fabric material, or a flexible foam, such as polyurethane or cross-linked polyethylene, and that is capable of having depressions permanently formed therein, as discussed further below. A preferred material for the barrier 6 is Volara™, available form Voltek Co., a division of Sekisui America Corp., Lawrence, Mass. The thickness of the barrier 6 when formed from a polymeric film is typically only 0.001 to 0.062 inch.

Generally, the barrier 6 is a single sheet of material having a width sufficient to form the garment facing surface 4 of the napkin. Preferably, the barrier 6 is longer and wider than the absorbent core 8 so that it extends around the sides of the core 8 in a C-shaped configuration so as to prevent leakage from the sides of the napkin. As shown in FIG. 2, the fluid impervious barrier 6 is joined to the cover 7, for example by an adhesive (not shown), around the perimeter of the napkin.

A pressure sensitive adhesive 10 is disposed on the garment facing surface 4 to allow the user to securely attach the napkin 1 to an under-garment. In the preferred embodiment, the pressure sensitive adhesive is of the hot melt type, such as an A-B-A block copolymer (i.e., styrene-ethylene-butylene-styrene block copolymer). By way of example, the pressure sensitive adhesive may be Fuller HM-6514, available from, H. B. Fuller Co., St. Paul, Minn.

According to the current invention, the pressure sensitive adhesive 10 is applied to the napkin 1 and protected from unintended contact prior to use in a novel way. Specifically, the adhesive 10 is applied in a pattern that allows discrete patches of adhesive to be distributed around the garment facing surface 4, as shown in FIG. 1, thereby more stably attaching the napkin 1 to the undergarment than if the adhesive were limited to the longitudinal center line of the napkin or in only a few discrete strips.

According to an important aspect of the current invention, each patch of adhesive 10 is disposed within a depression 9 formed in the barrier 6. In the preferred embodiment, the depressions 9 have a diameter at their openings in the range of approximately 0.1 to 0.5 inch and a depth in the range of approximately 0.1 to 0.25 inch. Placing the patches of adhesive 10 in the depressions 9 causes them to be integrally protected from unintended contact prior to use by the remaining portion of the barrier garment facing surface 4, that is, the portion that is between the depressions 9 and that is raised relative to them. To apply the napkin 1, the user merely removes it from its wrapper or package and then presses the under-garment against the garment facing surface 4 so that patches of pressure sensitive adhesive 10 contact the under-garment. In this regard, the barrier 6 is preferably sufficiently thin and flexible so that the depressions 9 can be deformed outward to allow the adhesive 10 to contact the under-garment. In addition, the diameter of the depressions 9 is sufficiently large to allow portions of the under-garment to enter the depressions so as to meet the adhesive 10. Thus, the good surface contact between the under-garment and the adhesive required for strong adhesion is assured.

As can readily be appreciated, the arrangement discussed above eliminates the need for release paper. The napkins can be stacked directly on top of one another in a box or individually wrapped for shipment and sale to the user without danger that the adhesive 10 will contact an adjacent napkin or the wrapping. The napkins can be stacked so that the garment facing surface 4 of one napkin rests against the adjacent napkin. Alternatively, each napkin can be folded so that the garment facing surface 4 on the front half of the napkin is in contact with the garment facing surface on the rear half of the napkin.

According to an important aspect of the current invention, the depressions 9, which in the preferred embodiment are conically shaped, must not only be flexible enough to allow them to be deformed outward when the napkin is pressed against the under-garment, so as to expose the adhesive, they must also have sufficient rigidity to prevent them from collapsing so easily that adhesive contact occurs during shipment or storage. The inventors have found that the depressions 9 will have sufficient rigidity if the barrier is formed from Volara™ having a thickness in the range of approximately 1/32 to 1/16 inch. The depressions can be further strengthened by pre-molding the absorbent core 8 so that it has similarly shaped depressions that support the barrier depressions 9. Alternatively, layers of other materials can be bonded or laminated to the barrier 6 before the depressions are formed in order to strengthen them.

In the preferred embodiment, the depressions 9 are created in the barrier 6 by a thermo-forming process. To this end, the barrier 6 is formed from a flexible thermoplastic material that can be permanently shaped by the application of pressure. The thermo-forming may be accomplished using a vacuum forming plate 13, shown in FIG. 3. The vacuum forming plate 13 has recesses 14 formed in its surface that match the depressions 9 to be formed in the barrier 6. Passages 15 formed in the plate 13 connect each recess 14 to a vacuum source 24. According to this method, a flat strip of barrier 6 material, preferably heated to approximately its glass transition temperature, is placed over the surface of the plate 13 with the surface 11 that is opposite to the garment facing surface 4 against the surface of the plate. Sufficient vacuum is then applied to the plate 13 so that the portions of the barrier 6 over the recesses 14 are locally sucked into the recesses. Such thermo-forming is best done before strip of barrier material has been cut into individual barriers. The recesses 14 are sized so that there is sufficient deformation in the barrier 6 to form permanent depressions 9 in the garment facing surface 4.

Figure 4:
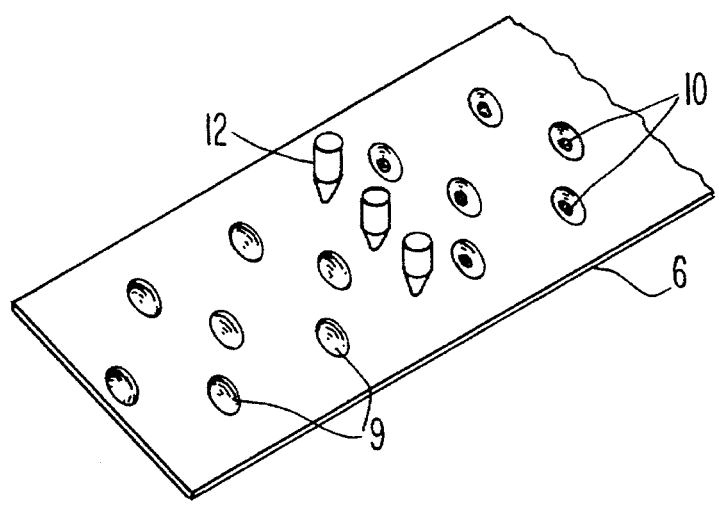
FIG. 4 is a schematic diagram of the portion of the production line for making the napkin shown in FIG. 1 that applies the adhesive to the barrier using nozzles.

As shown in FIG. 4, after the depressions 9 are formed, the barrier 6 is moved under a series of adhesive dispensing nozzles 12 that apply a patch of adhesive 10 into each depression. In the preferred embodiment, each patch of adhesive 10 has a diameter in the range of approximately 0.09 to 0.45 inch. If the napkin is to be folded for packaging, as discussed above, a groove or notch may also be thermo-formed into the barrier to facilitate such folding.

FIGS. 5a–c shown an alternate method for thermo-forming the depressions 9 in the barrier 6. In this approach, the barrier 6 is placed on the surface of the vacuum forming plate 13 as before except that the garment facing surface 4 itself is placed against the plate surface in which the recesses 14 are formed. As a result, a pattern of depressions 17 is formed in the surface 11 opposite the garment facing surface 4 and corresponding raised areas 16 are formed in the garment facing surface opposite each of the depressions 17, as shown in FIG. 5a. A patch of adhesive 10 is then applied on top of each raised area 16, as shown in FIG. 5b. The raised areas 16 are then inverted, for example, by placing the surface 11 onto the vacuum forming plate 13 and applying a vacuum that sucks the raised areas downward into the recesses 14. The result, as shown in FIG. 5c, is the formation of adhesive containing depressions 9 in the garment facing surface 4, as before. This approach facilitates manufacture since applying adhesive 10 patches to the raised areas 16 is easier than applying adhesive into the depressions 9 since the adhesive can be applied by wiping it onto the raised areas without the need for registration with each depression.

Figure 6:
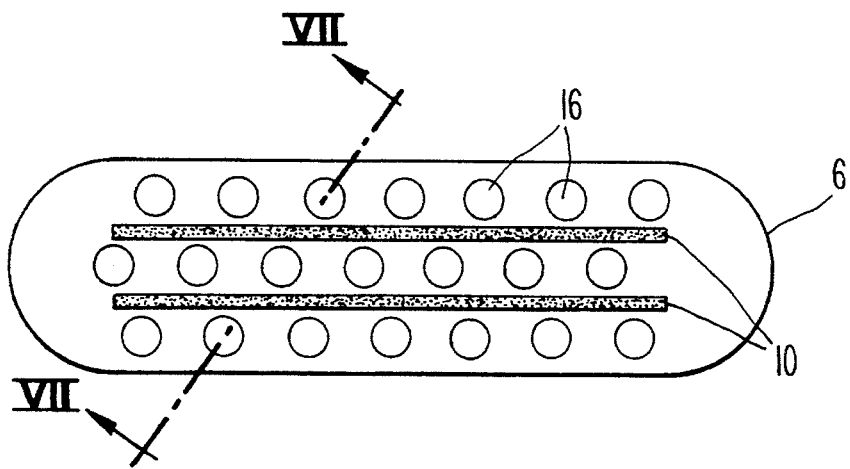
FIG. 6 is a plan view of the garment facing side of another embodiment of a sanitary napkin according to the current invention.
Figure 7:
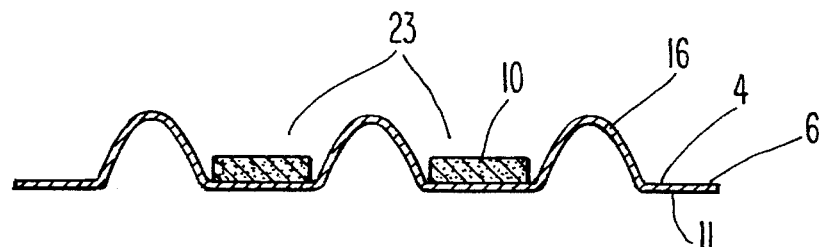
FIG. 7 is a cross-section through lines VII—VII shown in FIG. 6.

FIGS. 6 and 7 show another embodiment of the current invention. In this embodiment, a pattern of raised areas 16 is formed in the barrier garment facing surface 4 as before. In the preferred embodiment of this method, the raised areas are conically shaped and have a diameter in the range of approximately 0.1 to 0.5 inch and a height in the range of approximately 0.1 to 0.25 inch. The portions of the garment facing surface 4 between the raised areas 16 constitute recessed areas 23. In this approach, the adhesive 10 is applied to the recessed areas 23, for example by applying strips of adhesive 10, as shown in FIG. 6, so that the raised areas 16 serve to protect the adhesive prior to use.

Figure 8:
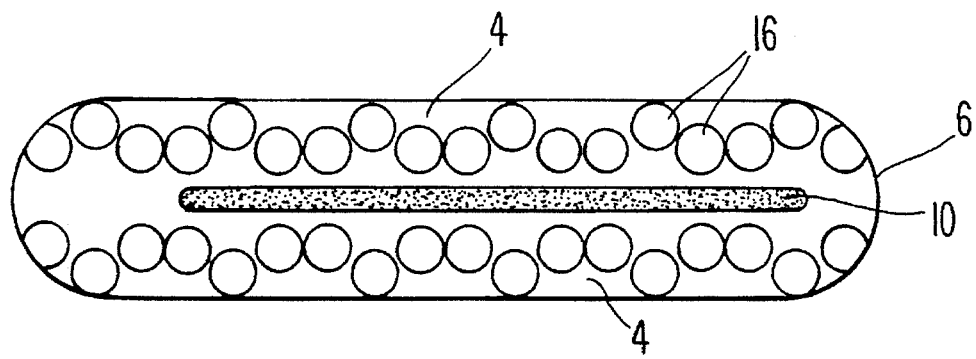
FIGS. 8 and 9 are plan views of the garment facing sides of two additional embodiments of the sanitary napkin according to the current invention.
Figure 9:
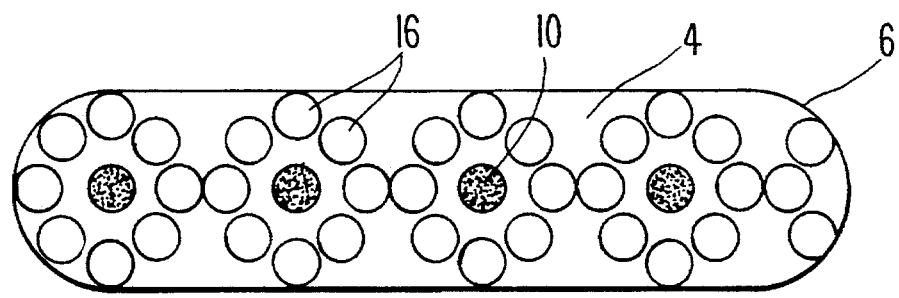

This method allows considerable flexibility in terms of the pattern of adhesive as well as the pattern of raised areas protecting the adhesive. FIG. 8 shows an embodiment of the napkin produced according to this method in which the adhesive pattern consists of a single strip of adhesive 10 extending along the longitudinal centerline of the barrier garment facing surface 4 and the raised area pattern consists of rows of raised areas 16 extending along the longitudinal edges of the barrier on either side of the adhesive strip. FIG. 9 shows another embodiment, in which a number of raised areas 15 surround each patch of adhesive 10 so that the adhesive and raised area patterns provide a decorative appearance, as well as protect the adhesive from unintended contact.

As previously discussed with respect to the depressions 9, in this embodiment the raised areas 16 must have sufficient rigidity to prevent them from collapsing during shipment and storage and thereby exposing the adhesive to contact prior to use.

Figure 10:
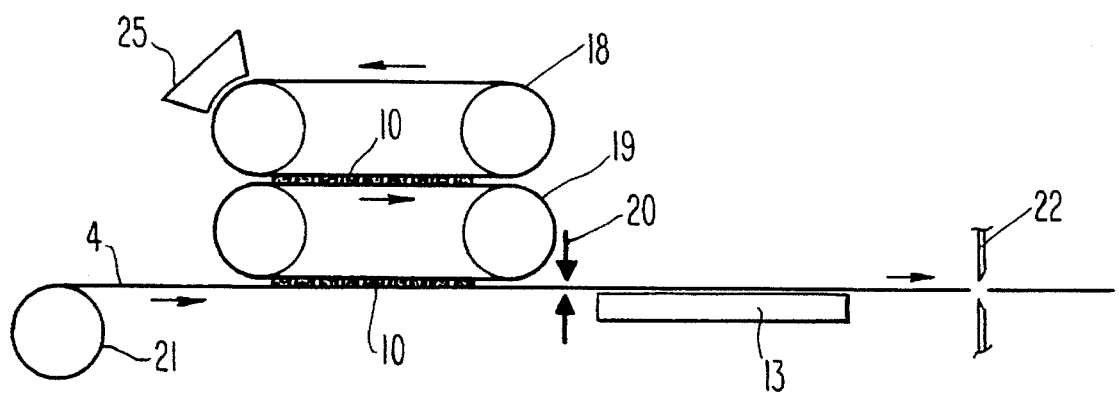
FIG. 10 is a schematic diagram of a portion of the production line for making the napkin shown in FIG. 1 that applies the adhesive to the barrier using a printing process.

FIG. 10 shows another embodiment of the method, in which a printing process is used to apply the adhesive pattern to the barrier garment facing surface 4. A printing belt 18 containing raised areas corresponding to the pattern of adhesive 10 to be applied receives adhesive from a printing device 25. The printing belt 18 then transfers the adhesive pattern onto a release belt 19 that has been coated—for example, with silicone—to reduce the bond between the adhesive 10 and the release belt 19 so that the adhesive will adhere to the barrier 6 material with greater tenacity than to the release belt. A strip of barrier 6 material from a roll 21, with its garment facing surface 4 facing upward, is then passed under the release belt 19 so that the adhesive 10 pattern is transferred to the garment facing surface.

After the adhesive 10 pattern has been applied, the barrier 6 material is passed over the vacuum forming plate 13. In this embodiment, the surface of the forming plate 13 contains a pattern of recesses 14 that matches that of the pattern of adhesive applied by the printing and release belts 18 and 19, respectively. Accurate registration between the adhesive 10 pattern and the pattern of recesses 14 in the forming plate 13 is accomplished via an electric eye device 13. The electric eye device 13 emits a beam of light that passes through the barrier material, which in this embodiment is a clear plastic film, but not the adhesive 10. The signal from the electric eye device 13 is used to stop the motion of the barrier material when the adhesive pattern is in the correct location over the plate 13—that is, when each of the patches of adhesive 10 is disposed above one of the recesses 14 in the forming plate.

When the barrier material is in place, vacuum is then applied to the forming plate 13, as before, to create a pattern of adhesive 10 containing depressions 9 in the garment facing surface 4, such as that shown in FIG. 5c. After vacuum forming, the strip of barrier 6 material is cut into individual barriers 6 in a cutting station 22. Alternatively, the vacuum plate 13 could be disposed above the barrier strip and the vacuum plate used to create raised areas in the garment facing surface between the adhesive, as shown in FIG. 7.

Use of the printing method of applying the adhesive 10 provides great flexibility in terms of the pattern of the adhesive applied to the barrier garment facing surface 4. This flexibility allows the adhesive 10 to be dispersed about the garment facing surface 4 in a pattern that optimizes the ability of the adhesive to stably secure the napkin to the undergarment. In addition, the printing method can be utilized in a print-embossing process in order to form and fill the depressions with adhesive.

Figure 11:
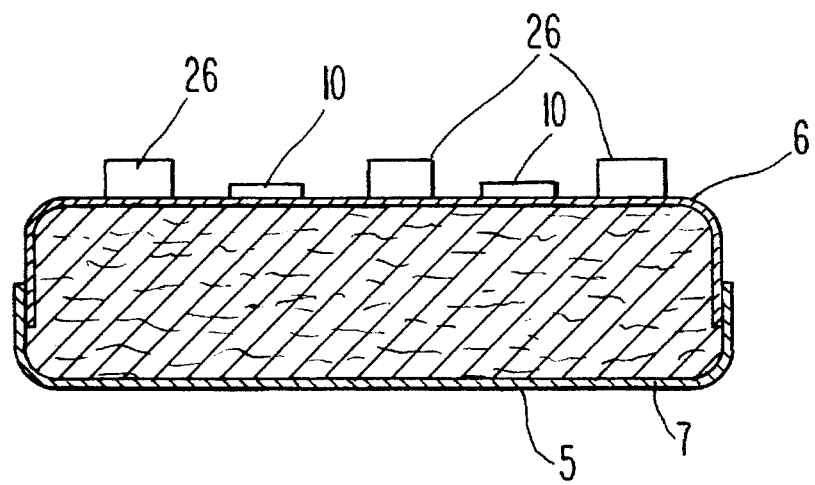
FIG. 11 is a transverse cross-section through another embodiment of the current invention.

FIG. 11 shows another embodiment of the invention in which two adhesives 10 and 26 are applied to the barrier garment facing surface 4. The adhesive 10 is a pressure sensitive adhesive, as before, that is applied in a pattern. The other adhesive 26 is a foaming non-pressure sensitive type adhesive. Such adhesives, which are preferably out-gassed, foam up after application to create areas that are raised above the surface of the pressure sensitive adhesive 10, as shown in FIG. 11. In the preferred embodiment, the thickness of the pressure sensitive adhesive 10 pattern is in the range of approximately 0.002 to 0.006 inch, whereas the thickness of the non-pressure sensitive adhesive 26 pattern, after the adhesive has foamed up, is in the range of approximately 0.003 to 0.007 inch. After the adhesive 26 has dried, its raised surfaces are capable of protecting the pressure sensitive adhesive 10 from unintended contact prior to use. According to the current invention, the adhesives 10 and 26 can be applied using either adhesive nozzles 12, such as those shown in FIG. 4, or a printing method, such as that shown in FIG. 10. However, the printing method has an advantage since the pressure between the adhesive nozzle and the surface of the barrier needed to ensure a clean stoppage of flow from the nozzle inhibits the foaming of the adhesive 26. Also, pressure may be applied to the pressure sensitive adhesive 10 by means of a contact roller to ensure that the non-pressure sensitive adhesive achieves a greater height.

Although the current invention has been discussed with reference to a sanitary napkin, the invention is also applicable to other types of absorbent products, such as panty liners and incontinence pads. Moreover, although the depressions in the barrier have been discussed as having been thermo-formed, other processes could also be used for permanently forming depressions in the barrier. Accordingly, the present invention may be embodied in other specific forms without departing from the spirit or essential attributes thereof and, accordingly, reference should be made to the appended claims, rather than to the foregoing specification, as indicating the scope of the invention.

What is claimed:

1. A method of applying and protecting positioning adhesive on an absorbent article having a fluid impervious barrier having a first surface forming a garment facing surface of such article and a second surface opposite said first surface, comprising the steps of:

a) deforming portions of said barrier so as to form a plurality of depressions in a pattern on said first surface of said barrier so as to form a corresponding raised area in said second surface of said barrier opposite each of said depressions; and b) depositing an adhesive within said depressions on said first surface of said barrier.

2. The method according to 1, wherein the step of forming said plurality of depressions in said pattern on said first surface of said barrier comprises applying a vacuum to said portions of said barrier.

3. The method according to 1, wherein said barrier is formed from a thermoplastic material, and wherein the step of deforming portions of said barrier comprises the step of applying heat and pressure to said barrier.

4. The method according to 3, wherein the step of applying heat to said barrier comprises heating said barrier to approximately its glass transition temperature.

5. The method according to 1, wherein the step of depositing said adhesive is performed using a printing process.

6. The method according to 1, wherein the step of depositing said adhesive is performed using nozzles.

7. The method according to 1, wherein said barrier is in the form of a continuous strip of material when said depressions are formed therein, and further comprising the step of cutting said strip of material into individual barriers after said depressions are formed.

8. A method of applying and protecting positioning adhesive on an absorbent article having a fluid impervious barrier having a first surface forming a garment facing surface of such article and a second surface opposite said first surface, comprising the steps of:

a) deforming portions of said barrier so as to form a plurality of depressions in a pattern on said second surface of said barrier, whereby said first surface has raised areas opposite each and corresponding to said depressions on said second surface and recessed areas in remaining portions of said first surface; and b) depositing an adhesive on said recessed areas of said first surface of said barrier.

9. The method according to 8, wherein the step of depositing said adhesive further comprises the step of depositing said adhesive in a line disposed on said first surface.

10. A method of applying and protecting positioning adhesive on an absorbent article having a fluid impervious barrier having a first surface forming a garment facing surface of such article and a second surface opposite said first surface, comprising the steps of:

a) deforming portions of said barrier so as to form a plurality of depressions in a pattern on said second surface of said barrier so as to form a corresponding raised area in said first surface of said barrier opposite each of said depressions;

b) depositing an adhesive onto said raised areas; and c) inverting each of said depressions and said raised areas so as to form adhesive containing depressions in said first surface of said barrier and raised areas in said second surface.

11. The method according to 10, where the step of inverting said raised areas comprises the step of applying a vacuum thereto.

12. A method of making an absorbent article having a fluid impervious barrier that forms a garment facing surface of said article, comprising the steps of:

a) depositing a pressure sensitive adhesive in a first pattern on said garment facing surface of said barrier; and b) depositing a non-pressure sensitive foaming adhesive in a second pattern on said garment facing surface of said barrier, said non-pressure sensitive foaming adhesive foaming to a thickness greater than said pressure sensitive adhesive so as to form areas raised above said pressure sensitive adhesive and said second pattern provides sufficient void areas to expose said pressure sensitive adhesive.

13. The method according to 12, wherein the steps of depositing said pressure sensitive adhesive and said non-pressure sensitive foaming adhesive are performed using a printing press.

14. A method of applying and protecting positioning adhesive on an absorbent article having a fluid impervious barrier having a first surface forming a garment facing surface of such article and a second surface opposite said first surface, comprising the steps of:

transferring said adhesive from a reservoir onto a release surface in a pattern, said adhesive capable of bonding to said barrier with greater tenacity than to said release surface;

transferring said adhesive from said release surface onto said first surface of said barrier in said pattern; and deforming portions of said barrier so as to form a plurality of depressions in said pattern on said first surface of said barrier so as to form a corresponding raised area in said second surface of said barrier opposite each of said depressions;

wherein said adhesive is located in said depressions.

15. The method according to 14, wherein the step of transferring said adhesive from said reservoir onto said release surface comprises printing said adhesive in said second pattern onto a first belt.

16. The method according to 15, wherein the step of transferring said adhesive from said reservoir onto said release surface further comprises transferring said adhesive in said pattern from said first belt onto a second belt on which said release surface is formed.

17. The method according to 14, wherein the step of forming said plurality of depressions in said barrier is performed after said adhesive has been transferred to said barrier.

* * * * *

UNITED STATES PATENT AND TRADEMARK OFFICE
CERTIFICATE OF CORRECTION

PATENT NO. : 5,453,296
DATED : Sept. 26, 1995
INVENTOR(S) : Nels J. Lauritzen and John T. Ulman It is certified that error appears in the above-indentified patent and that said Letters Patent is hereby corrected as shown below:

Claim 13, line 12, col. 9, the word "press" should be

--process --.

Signed and Sealed this

Twelfth Day of November, 1996

Attest:

BRUCE LEHMAN

Attesting Officer     Commissioner of Patents and Trademarks